United States Patent
Schroeder et al.

(10) Patent No.: US 6,520,033 B1
(45) Date of Patent: Feb. 18, 2003

(54) APPARATUS FOR SAMPLING & ANALYSIS OF THERMALLY-LABILE SPECIES AND A METHOD RELATING THERETO

(75) Inventors: William H. Schroeder, Ontario (CA); Julia Lu, Ontario (CA)

(73) Assignee: Her Majesty the Queen in right of Canada, represented by the Minister of the Environment, Ottawa (CA)

( * ) Notice: Subject to any disclaimer, the term of this patent is extended or adjusted under 35 U.S.C. 154(b) by 0 days.

(21) Appl. No.: 09/538,136

(22) Filed: Mar. 29, 2000

(51) Int. Cl.[7] .............................. G01N 1/18; G01N 1/20; G01N 1/24; G01N 1/40

(52) U.S. Cl. ........................ 73/863.12; 73/863.23; 73/31.07; 73/64.56

(58) Field of Search .................... 73/863.12, 863.23, 73/863.24, 863.25, 31.07, 64.56

(56) References Cited

U.S. PATENT DOCUMENTS

| | | | | | |
|---|---|---|---|---|---|
| 3,667,688 | A | * | 6/1972 | Iannicelli .......................... 241/1 |
| 3,933,431 | A | * | 1/1976 | Trujillo et al. ........ 73/863.21 X |
| 4,759,210 | A | * | 7/1988 | Wohltjen .................... 73/31.07 |
| 4,977,095 | A | * | 12/1990 | Zaromb ............... 73/864.81 X |
| 5,493,923 | A | * | 2/1996 | Balfanz et al. ....... 73/863.12 X |
| 5,585,529 | A | * | 12/1996 | Corbin et al. ................. 570/179 |
| 5,599,764 | A | * | 2/1997 | Sharma et al. ............... 502/417 |
| 5,660,795 | A | * | 8/1997 | Schaedlich et al. ............ 402/88 |
| 5,690,529 | A | * | 11/1997 | Oberpriller et al. ..... 73/31.07 X |
| 6,192,766 | B1 | * | 2/2001 | Gärdhagen et al. ....... 73/863.12 |
| 2002/0007687 | A1 | * | 1/2002 | Zimmermann et al. .. 73/864.71 |

FOREIGN PATENT DOCUMENTS

| | | | | |
|---|---|---|---|---|
| DE | 3221570 A1 | * | 12/1983 | .................. 210/495 |
| EP | 309007 A1 | * | 3/1989 | .......... G01N/31/12 |
| EP | 588664 A2 | * | 3/1994 | ............ G01N/1/28 |

OTHER PUBLICATIONS

Keeler, G.J., Glinsorn, G., and Pirrone, N., 1995, *Water, Air, Soil Pullut.* 80, 159–168, Month Not Given.

Guentzel, J.L., Landing, W.M., Gill, G.A., and Pollman, C.D.: 1995, *Water, Air, Soil Pollut.* 80,393–402, Month Not Given.

Fitzgerald, W.F., Mason, R.P., and Vandal, G.M.: 1991, *Water, Air, Soil Pollut.* 56, 745–767, Month Not Given.

Brosset, C., and Lord, E.: 1991, *Water, Air, Soil Pollut.* 56, 493–506, Month Not Given.

Ebinghaus, R., Jennings, S.G., Schroeder, W.H., Berg, T., Donaghy, T., Ferrara, R., Guentzel, J., Kenny, C., Kock, H.H., Kvietkus, K., Landing, W., Mazzolai, B., Mühleck, T., Munthe, J., Prestbo, E.M., Schneeberger, D., Slemr, F., Sommar, J., Urba, A., Wallschläger, D., and Xiao, Z.: 1998, *Atmos. Environ.*, Atmospheric Environment 33 (1999) 3063–3073, Month Not Given.

Schroeder, W.H., Keeler, G., Kock, H.H., Roussel, P., Schneeberger, D., and Schaedlich, F.: 1995, *Water, Air, Soil Pollut.* 80, 611–620, Month Not Given.

Lu, J.Y., Schroeder, W.H., Berg, T., Munthe, J., Schneeberger, D., and Schaedlich, F.: *Anal. Chem.* 70, 2403–2408, June 1998.

P. Solomon et al. Journal of the Air Pollution Central Association Apr. 1982 vol. 32, No. 4 pp. 373–375.

\* cited by examiner

*Primary Examiner*—Thomas P. Noland
(74) *Attorney, Agent, or Firm*—McFadden, Fincham

(57) ABSTRACT

An apparatus for, and a method of, sampling and analyzing thermally-labile chemical species, comprises a quartz tube having a filter member positioned in the bore of the tube. The filter member comprises a plug of quartz beads having a layer of quartz frits on either side. A fluid (gas or liquid) carrying one or more chemical substances associated with particulate matter is passed through the tube, the particulate material being collected by the quartz beads. After sample collection, the material remaining/retained from the original sample is removed, as for example by thermal desorption, and the material is then analyzed.

12 Claims, 2 Drawing Sheets

APPARATUS FOR SAMPLING & ANALYSIS OF THERMALLY-LABILE SPECIES AND A METHOD RELATING THERETO

FIELD OF THE INVENTION

This invention relates to an apparatus for sampling and analysis of thermally-labile species, such as mercury, arsenic, selenium, sulfur, lead, carbon, polyaromatic hydrocarbons, n—alkanes and the like, as may be associated with a variety of solid matrices (e.g., airborne particulate matter, suspended particles, soil materials, colloids). The invention also relates to a method of carrying out such sampling and analysis.

BACKGROUND OF THE INVENTION

Various technologies exist for either collecting or separating particulate material from a fluid flow such as a gaseous stream. Such devices include filter packs which collect the material(s) of interest and the filter(s) then being treated as, for example, by using one or more acids or oxidation reagents, with the resulting final solution then being analyzed. In another example, a quartz wool stationary phase is used to retain particulate material on a manually-loaded plug contained in a quartz tube. The tube, along with the collected sample, are heated to an elevated temperature and the released elements of interest are detected and quantified. Yet another example is a miniaturized device using a quartz fiber filter disc. Particulate material, suspended in one or more gases or liquids, is trapped on the filter disc, following which the device is heated and the released elements detected and quantified.

When using filter packs, "clean hands" techniques and a clean-room facility are necessary for accurate results. Furthermore, ultra pure reagents, which are expensive, are required in those procedures involving sample treatment prior to analysis. This mode of operation is, therefore, time consuming and costly. Quartz wool plugs are difficult, if not impossible, to prepare uniformly. Hence, collection efficiency may vary from plug to plug. More importantly, sorption of gaseous species, for example elemental mercury vapor by the quartz wool, may generate erroneously high results in the determination of "particulate-phase mercury" in air. Miniaturized devices with a quartz fiber disc overcome the disadvantages of quartz wool plugs, but the filter disc becomes brittle after being heated at a high temperature, for example over 900° C. A fresh filter disc is therefore required for each sample. Hence it is difficult to automate the whole measurement procedure, including sampling and sample analysis.

With prior art technologies, e.g. quartz wool plugs, it is a major problem to collect particles of sub-micron size in such a way that uniform and consistent sampling is obtained. It is a further problem to provide an efficient automated and economical procedure.

SUMMARY OF THE INVENTION

The present invention provides a novel apparatus, and a method, which is efficient, economical and which can be easily automated. In accordance with the present invention, there is provided a device for trapping particulate material in a fluid (usually/generally gaseous) stream, such as ambient air, or other fluid media, together with a pyrolyzer for sample pre-treatment prior to analysis. Thus, the present invention is suitable for sampling and analyzing mercury, for example, as well as other thermally-labile species. Broadly, a device of the present invention comprises a quartz housing with a filter member having a quartz bead plug and bead retainers such as quartz frits positioned on either side of the quartz beads. The housing, preferably in the form of a tube, is variable in length and in width. The porosity of the bead plugs may vary, as desired, depending on the size range of the particulate matter to be collected. The dimensions of the plug can vary as can the pore size of the quartz frits.

In the method in accordance with the inventions, a filter member comprising a quartz bead plug having quartz frits on either side thereof is loaded into a quartz housing e.g. a tube. A flow of fluid gas, for example air containing airborne particulate material, is passed through the tube with particulate material being collected in the quartz bead plug. After passage of the fluid, the whole unit may be positioned in a heating chamber where the tube and filter member are heated to a high temperature, for example up to 900° C. or up to 1200° C., for thermal desorption and subsequent analysis of the collected material by an analyzer located downstream of the sampling unit.

BRIEF DESCRIPTION OF THE DRAWINGS

The invention will be readily understood by the following description of certain embodiments, by way of example, in conjunction with the accompanying drawings in which.

BRIEF DESCRIPTION OF THE PREFERRED EMBODIMENTS

Figure 1:
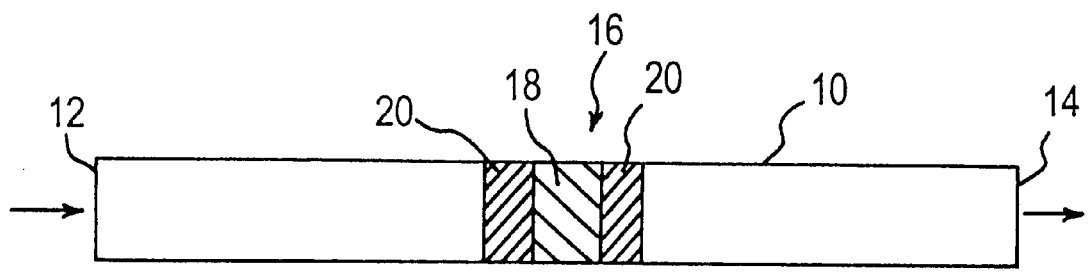
FIG. 1 diagrammatically illustrates one form of a device.

As shown in FIG. 1, an apparatus comprises a quartz tube 10, having an inlet 12 and an outlet 14. Centrally positioned in the tube 10 is a filter member or element designated generally as 16, having a central plug 18 of quartz beads with a layer quartz frit 20 on each side. Thus, fluid flow enters at inlet 12 as indicated, exiting at 14. During passage through the member 16, particulate material in the gas (or liquid) is retained on the quartz beads. After a predetermined volume of fluid flows through the filter member 16, the flow is cut off. The tube 10 and contained member 16 is then heated to, to a selected temperature for example, 1200° C. The chemical species of interest, which are associated with the particulate material on the beads, are thermally desorbed (either slowly or rapidly depending upon the rate of heating of the apparatus).

The tube 10 is normally connected to an analyzer 22 and the tube itself can be positioned in a heating enclosure, for example, a suitable housing as indicated at 24, for the heating thereof. To this end, any suitable heating device may be employed; preferably, the means of heating is a heater which surrounds the quartz housing or tube and may be in the form of heating wires, an infrared heating device, or a suitable microwave oven or cavity.

The diameter and length of the tube 10 will vary depending upon the specific application. The larger the tube, the higher the flow rate, but too large a tube can result in insufficient heating, particularly at the center of the filter member 16, as well as reducing the rate at which the tube is heated. In one example, the tube has a bore of between 10 and 20 mm., with the filter member 16 having a length of about 2 mm.

As noted above, the size of the quartz beads can vary depending upon the specific application. As a general rule, the smaller the particle size of the particulate matter to be collected, the smaller the size of the beads. The length of the quartz bead plug 18 should be long enough to retain all particulate material in the desired size range. Typically, the particulate filtration medium 18 may be in the form of quartz or ceramic beads which have a size of from about 8 to about 170 mesh, and more desirably from about 40 mesh to about 120; or between 80 and 170 mesh.

Also, the porosity of the quartz frits can vary depending upon the specific application. As a general rule, the pore size of the quartz frits 20 should be smaller than the size of the quartz beads 18. Typically, the porosity of the quartz frits will vary from a porosity value in the range of 00 to 4. Suitable quartz frits are commercially available from Heraeus Amersil Inc.

In a preferred embodiment of the invention, where the quartz frits are in a quartz housing, the quartz frits may be sintered to the quartz housing. The frits are fused to the interior bore of the housing, with a space there between within which quartz or ceramic beads are packed. The bead plug is thus effectively integrated with the quartz housing.

Figure 2:
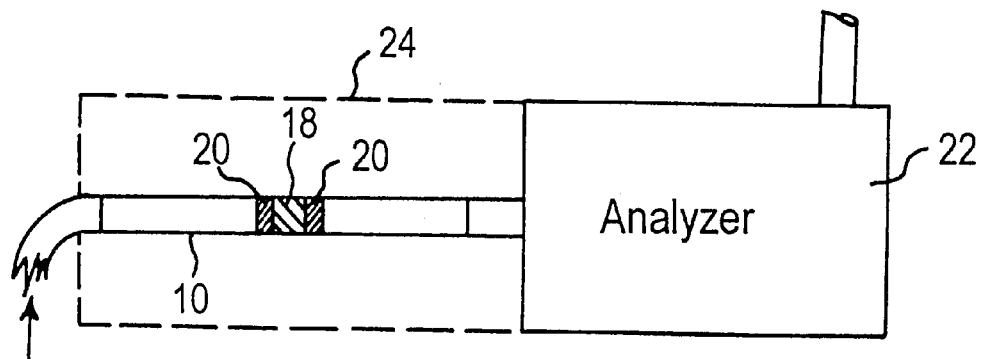
FIG. 2 is a diagrammatic illustration of a system embodying a device as in FIG. 1.

The method of operation according to the present invention is generally as follows (with reference to FIG. 2). A fluid, for example, air containing suspended particulate matter is drawn (with a suitable pump or other flow creating device) through the tube 10, with the particulate matter being retained on the quartz of beads. After a predetermined volume of air, or other fluid medium, has been sampled, the flow is shut off. The tube and filter member now containing the sample, is connected to an analyzer 22 and is then heated to thermally desorb the material collected on the quartz or ceramic filter media. The species released are then passed through the analyzer 22 for the purpose of qualitative and/or quantitative chemical analysis.

Figure 3:
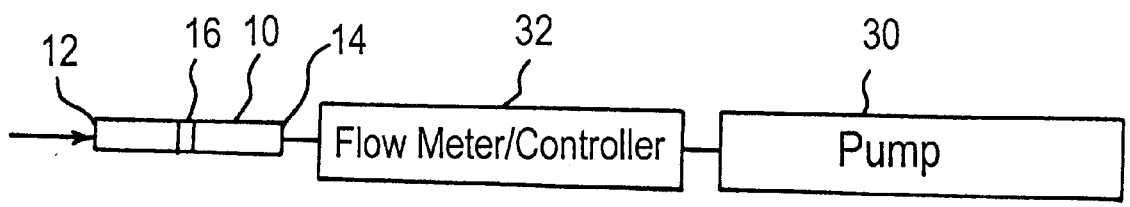
FIGS. 3, 4 and 5 illustrate diagrammatically slightly different systems as further examples. Common reference numerals are used where applicable.

FIG. 3 illustrates a system for collecting particulate matter suspended in a fluid medium. Ambient air, as an example, is drawn through the filter device, the flow being produced by a pump 30 and passed through a flow meter/controller 32 to measure/regulate the flow rate of the fluid medium.

Figure 4:
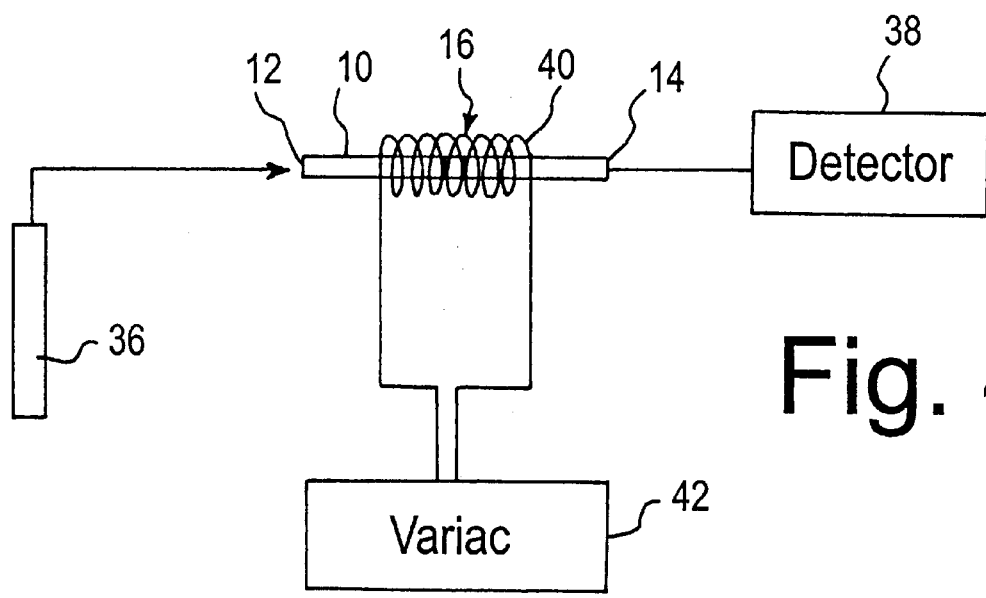

After collection, the filter device is connected (in reverse) to an analytical system, as shown in FIG. 4. The filter device, including the collected sample, has a carrier gas supply, for example from a cylinder 36 through a detection device 38. Any suitable detector may be employed for quantifying and/or identifying the species to be analyzed. For example, a detector for mercury can be a commercially available cold vapor atomic fluorescence spectrometer (CVAFS). A heater 40 surrounds the filter device. The heater is controlled by a variable transformer (Variac) 42. A suitable carrier gas for mercury is, for example, argon, and a suitable detector would be a conventional CVAFS tuned to 253.7 nm in the case of mercury. On heating, the sample on the filter device will be thermally released and detected.

In a manual approach for the determination of particulate-phase mercury in ambient air, airborne particulate matter is collected on the precleaned quartz medium at a flow rate ranging from 3 to 5 L/min. After twelve hours of sampling, the device, along with the sample, is connected to an analytical train, similar to that shown in FIG. 4. The device is then heated to 900° C. for 5 minutes and the released mercury species are carried downstream by argon gas at a flow rate of 200 ml per min. to a TEKRAN® mercury vapor analyzer, where the mercury (and/or other constituents) in the sample is/are quantified.

Figure 5:
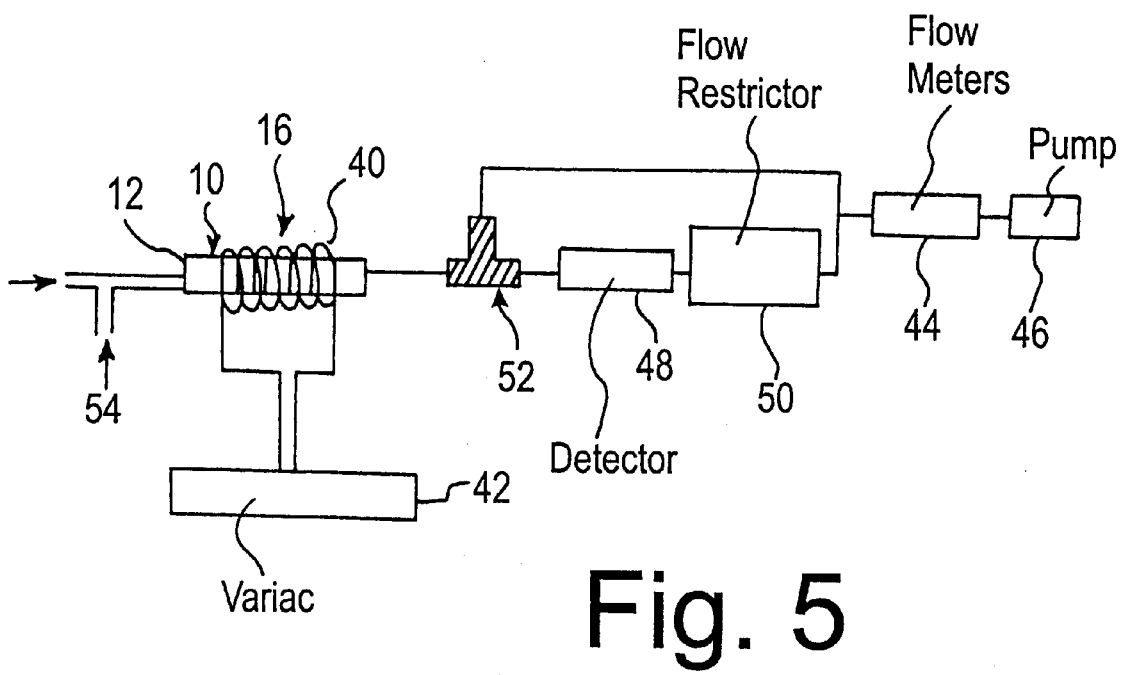

The systems of FIGS. 3 and 4 can be combined, as shown in FIG. 5. Air is drawn through the filter device and the flow meters of 44 via a pump 46. Particulate matter is collected or retained on the filter member. After collection of a sample, the valve 52 is actuated to close off direct connection to the flow meter, and thus permit flow through the detector 48 and flow restrictor 50. Carrier gas is supplied from a gas cylinder or other source, at inlet 54. The filter device is heated by heater 40 and the released species are detected/determined by the detector 48. Such a system as illustrated in FIG. 5 can be operated manually or automatically.

The apparatus described herein can be used for sampling and analysis of not only particulate-phase mercury but also any thermally-labile particulate species (chemical substance/element or compound) that can be thermally desorbed at, or below, a temperature of 1200° C. Typical of such species are those identified above.

For example, a suitable commercial mercury analyzer can be used for fully automated monitoring of mercury associated with airborne particulate matter. Likewise, any suitable commercial carbon (or multi-element) analyzer can be used for determination of the total carbon (as well as other elemental or molecular species) associated with airborne particulate matter. Similarly, any commercial detector with proper interfacing can be used for determination of thermally-labile species associated with particulate matter in ambient air.

The invention provides for both sampling and analysis of thermally-labile species associated with airborne particulate matter (i.e., the sample) without direct handling, transfer and preparation of the sample. The actual filtering device, that is the tube with the filter member supported by quarts frits, is entirely reusable. This makes possible the automated monitoring of mercury and other thermally-labile species associated with airborne particulate matter, for example, by connecting the apparatus of the present invention as a front-end device on a TEKRAN® automated mercury analyzer.

The use of quartz or ceramic beads and frits of this invention, instead of conventional filter packs and quartz wool plugs according to the prior art, thus provides numerous distinct and significant advantages including the fact that the device is entirely reusable, easily cleaned, and sampling and analysis procedures are less time-consuming as well as being less costly. Automation (of sampling and/or analysis) is also possible and the sample collection apparatus is chemically inert and can withstand high temperatures.

The sampling apparatus of this invention has an all quartz construction and no corrosive parts or components, thus making it chemically inert. It is, therefore, resistant to organic or inorganic acids and many other normally reactive chemicals. It is thus also suitable for filtration of corrosive gases and liquids containing suspended solids.

The apparatus of the present invention is quickly assembled and easily decontaminated by thermal means and other types of treatment, thus avoiding the use of toxic or environmentally unfriendly cleaning agents/reagents/hazardous solutions or the like. Thus, the method and apparatus of the present invention can achieve ultra-trace analytical detection limits and extremely low (sub-ppt) operational analytical blanks. Furthermore, the sampling device is suitable for high temperature applications and the quartz tube 10 is of a transparent nature, allowing easy visual inspection and direct observation of the sample at all stages. The beads (uniform in diameter) give a precise pore size distribution and function as a good heat diffuser by having a large surface area conducive to heat distribution.

The present invention overcomes the disadvantages of the generally known existing techniques (a) filter packs, (b) quartz wool plugs and (c) fiber discs or mats. Filter packs generally contain one or more membrane filter(s) of 47 mm diameter or larger, which are precleaned using acid solutions, or heating, depending upon the filter medium. The filters are then manually loaded into the filter holder. After sampling, the sample collected on the filter medium (e.g. cellulose (filter paper), polyethylene, "Teflon", glass fiber or quartz fiber) is transferred, along with the filter, into either a container where it is extracted or digested using acids or mixtures of activation reagents (with or without ultrasonication) followed by analysis, or alternatively a chamber for thermal desorption, followed by identification and quantification. For accurate results, when using a conventional or traditional trace or ultra-trace measurement procedure, a "clean hands" technique and a clean-room facility are essential. Ultra-pure reagents, a necessity for traditional approaches are costly. The conventional procedure is time consuming and expensive to operate.

For quartz wool plugs, the particulate matter is retained (at an unknown collection efficiency) by the quartz wool plug and then the apparatus is heated to a high temperature, the released elements detected and quantified. It is very difficult, if not impossible, to prepare wool plugs uniformly and thus collection efficiency can vary from plug to plug. Absorption of gaseous forms of the element(s) of interest (e.g. Hg° vapor in the case of determining particulate—phase mercury) by the quartz wool during the sample collection step can generate erroneously high results.

Other devices, such as those employing a quartz fiber disc, trap particulate material on the disc. The disc, with collected sample, is heated to a high temperature and released elements detected and quantified. Although overcoming the disadvantages of quartz wool plugs, the quartz fiber filter disc will become brittle after heating and therefore a fresh disc is required for each sample, making it difficult to automate the whole procedure.

Thus the invention provides for a reusable member, having a consistent bead size for consistent trapping. It is not detrimentally affected by heat or by other extraction/desorption steps, for example, such as corrosive acids or other hazardous reagents. The bead size can be optimized for any particulate material to be collected. The easy and effective cleaning feature and reusability provide for an economical system capable of complete automation.

The present invention, when using quartz beads, provides the flexibility to adjust bead size to suit the particulate matter to be collected, thus ensuring high efficiency of retention during the sampling step.

We claim:

1. A method of sampling and analyzing thermally-labile species, comprising: positioning a filter member in a quartz housing, said filter member comprised of a particulate filtration medium held in place by quartz frits associated with said filtration medium; feeding a fluid containing one or more thermally-labile species through said housing; retaining said thermally-labile species on said particulate filtration medium; removing the retained species from said particulate filtration medium through thermal desorption and analyzing the removed species.

2. A method as claimed in claim 1, including removing said retained species by heating to an elevated temperature to desorb said retained species.

3. A method as claimed in claim 2, including heating to a temperature of between about 900° C. and about 1200° C.

4. A method as claimed in claim 1, said fluid comprising a gas or a liquid.

5. A method as claimed in claim 1, including analyzing said retained species by feeding through an analyzer.

6. A method as claimed in claim 5, wherein said analyzer is an analyzer for a specific element.

7. A method as claimed in claim 5, wherein said analyzer is a multi-element analyzer.

8. A method as claimed in claim 1, said particulate filtration medium comprising quartz or ceramic beads.

9. A method as claimed in claim 8, said beads having a size of about 8 to about 170 mesh.

10. A method as claimed in claim 9, said beads having a size of about 40 to about 120 mesh.

11. A method as claimed in claim 1, said quartz frits having a porosity in the range of about 00 to 4.

12. A method as claimed in claim 1, said filter member having a length of about 2 mm and said housing having a bore of about 10 mm to about 20 mm.

* * * * *